United States Patent [19]  [11]  4,293,648
Davino  [45]  Oct. 6, 1981

[54] PROCESS FOR ESTERIFICATION OF α-L-ASPARTYL-L-PHENYLALANINE

[75] Inventor: Arthur A. Davino, Skokie, Ill.

[73] Assignee: G. D. Searle & Co., Skokie, Ill.

[21] Appl. No.: 183,556

[22] Filed: Sep. 2, 1980

Related U.S. Application Data

[63] Continuation-in-part of Ser. No. 102,807, Dec. 12, 1979, abandoned, which is a continuation-in-part of Ser. No. 27,196, Apr. 5, 1979, abandoned.

[51] Int. Cl.³ .............................................. C12P 21/02
[52] U.S. Cl. ..................................... 435/70; 435/128; 435/135
[58] Field of Search .......................... 435/70, 128, 135

[56] References Cited

PUBLICATIONS

Ingalls et al., Biotechnology & Bioengineering, vol. 17, pp. 1627–1637 (1975).
Klibanov et al. Biotechnology & Bioengineering, vol. 19, pp. 1351–1361 (1977).

Primary Examiner—Lionel M. Shapiro
Attorney, Agent, or Firm—Mary Jo Kanady; James G. Passé

[57] ABSTRACT

A process for selectively esterifying α-L-aspartyl-L-phenylalanine to the corresponding alkyl esters using a proteolytic enzyme with specific esterase activity is described. The process is carried out in an aqueous-alcohol medium in which the alcohol concentration is sufficient to reverse the esterase activity. The α-L-aspartyl-L-phenylalanine alkyl esters so produced are useful as artificial sweeteners.

12 Claims, No Drawings

PROCESS FOR ESTERIFICATION OF α-L-ASPARTYL-L-PHENYLALANINE

This application is a continuation-in-part of U.S. application Ser. No. 06,102,807 filed Dec. 12, 1979 which is a continuation-in-part of U.S. application Ser. No. 27,196, filed Apr. 5, 1979, both now abandoned.

BACKGROUND OF THE INVENTION

1. Field of the Invention

The present invention relates to a process for selectively esterifying α-L-aspartyl-L-phenylalanine to the corresponding alkyl esters using a proteolytic enzyme having specific esterase activity.

2. Description of the Prior Art

The esterification of α-L-aspartyl-L-phenylalanine by chemical means has been described in U.S. Pat. Nos. 3,933,781 and 4,173,562. A disadvantage of chemical methods is that esterification occurs at the aspartyl carboxyl group as well as at the phenylalanine carboxyl group so that undesirable by-products of formula I of chart A (hereinafter referred to as the diester) and formula II of chart A (hereinafter referred to as the aspartyl ester) are formed.

The diester and the aspartyl ester must be removed by purification steps in order to obtain the desired product.

Previous enzymatic esterification procedures have been directed to the esterification of single amino acids. They have not been concerned with the selective esterification problems that occur with dipeptides, particularly α-l-aspartyl-L-phenylalanine which has more than one carboxyl group.

For example, Ingalls, et al., BIOTECHNOLOGY AND BIOENGINEERING 17, 1627–1637 (1975) describes the esterification of a single amino acid, N-acetyltyrosine, using immobilized chymotrypsin or subtilisin Carlsberg in the free, unmodified form in a solvent system of water, ethanol and glycerol. A disadvantage of this method was that significant amounts of the glycerol ester of the amino acid were formed.

Klibanov, et al., BIOTECHNOLOGY AND BIOENGINEERING 19, 1351–1361 (1977) describes the esterification of a single amino acid, N-acetyltryptophan using immobilized chymotrypsin in a biphasic system of water and a water-immiscible solvent, chloroform.

An advantage of the present invention is that the carboxyl group of the phenylalanine moiety is selectively alkylated by enzymatic esterification in a single phase system to give α-L-aspartyl-L-phenylalanine alkyl ester without producing the undesireable diester and aspartyl ester. This is accomplished by contacting the dipeptide with an alcohol in the presence of a serine alkaline proteinase, an esterase exhibiting a preference for aromatic amino acids.

SUMMARY OF THE INVENTION

The present invention relates to a process for the preparation of α-L-aspartyl-L-phenylalanine alkyl esters which are useful as sweetening agents. In particular, the dipeptide, α-L-aspartyl-L-phenylalanine is esterified by contacting the dipeptide with an alcohol in the presence of proteolytic enzyme having specific esterase activity in a water-alcohol solvent system in which the alcohol concentration is sufficient to reverse the hydrolytic action of the enzyme. Specific esterase activity refers to the proteolytic enzyme's ability to selectively alkylate the carboxyl group of the phenylalanine moiety. α-L-aspartyl-L-phenylalanine alkyl esters so produced are useful as sweetening agents. This utility has been described in U.S. Pat. No. 3,492,131.

Alternatively, N-protected-α-L-aspartyl-L-phenylalanine may be esterified by this process to give the corresponding N-protected-α-L-aspartyl-L-phenylalanine alkyl ester. The N-protecting group can be removed by conventional techniques to give α-L-aspartyl-L-phenylalanine alkyl ester. A preferred N-protecting group for use in this invention is the carbobenzoxy group.

DESCRIPTION OF THE PREFERRED EMBODIMENTS

The present invention relates to a process for selectively esterifying α-L-aspartyl-L-phenylalanine by contacting α-L-aspartyl-L-phenylalanine or N-protected-α-L-aspartyl-L-phenylalanine with an alcohol in the presence of a proteolytic enzyme having specific esterase activity. The dipeptide is contacted with the enzyme in an aqueous-alcohol medium in which the alcohol concentration is sufficient to reverse the hydrolytic activity.

According to the present invention there is provided a process for esterifying α-L-aspartyl-L-phenylalanine which comprises contacting α-L-aspartyl-L-phenylalanine or N-protected-α-L-aspartyl-L-phenylalanine with an alcohol in the presence of an effective esterifying amount of a serine alkaline proteinase in an aqueous-alcohol medium in which the alcohol concentration is sufficient to reverse the hydrolytic activity of the serine alkaline proteinase. When N-protected α-L-aspartyl-L-phenylalanine is esterified, the N-protecting group is removed following esterification to give the α-L-aspartyl-L-phenylalanine alkyl ester.

Preferred alcohols are represented by the formula

R—OH where R is lower alkyl having 1–7 carbon atoms. These lower alkyls are exemplified by methyl, ethyl, propyl, butyl, pentyl, hexyl, heptyl and the branched chain isomers thereof.

The amino group of α-L-aspartyl-L-phenylalanine may be protected by commonly used protecting groups. Such groups include, but are not limited to aryl-lower alkyl groups, such as diphenylmethyl or triphenylmethyl groups which may be optionally substituted by halogen, nitro, lower alkyl or lower alkoxy, for example; benzhydryl, trityl, and di-paramethyoxybenzhydryl; acyl groups, such as formyl, trifluoroacetyl, phthaloyl, benzenesulphenyl and o-nitrophenylsulphenyl; groups derived from carbonic acid or thiocarbonic acid, such as carbobenzoxy groups which are optionally substituted in the aromatic radical by halogen atoms, nitro groups or lower alkyl, lower alkoxy or lower carboalkoxy groups, for example, carbobenzoxy, p-bromocarbobenzoxy or p-chlorocarbobenzoxy, p-nitrocarbobenzoxy and p-methoxycarbobenzoxy; coloured benzyloxycarbonyl groups such as p-phenylazobenzyloxycarbonyl and p-(p-methoxyphenylazo) benzyloxycarbonyl, tolyloxycarbonyl, 2-phenyl-2-propoxycarbonyl, 2-tolyl-2-propoxycarbonyl and 2-(parabiphenylyl)-2-propoxycarbonyl; and aliphatic oxycarbonyl groups, such as t-butoxycarbonyl, alkyloxycarbonyl, cyclopentyloxycarbonyl, t-amyloxycarbonyl. A particularly preferred N-protecting group for use in this invention is the carbobenzoxy group.

The amino groups can also be protected by forming enamines, obtained by reaction of the amino group with 1,3-diketones, for example benzoylacetone, or acetylacetone.

Protecting groups are conveniently removed by reactions such as hydrogenolysis (for instance, in the presence of a palladium black catalyst), treatment with a hydrohalo acid (such as hydrobromic, hydrofluoric or hydrochloric acids) in acetic acid, or treatment with trifluoroacetic acid.

The reaction in which the ester bond is formed can be conducted in an aqueous buffer-alcohol solution having a pH which maintains enzyme activity. This is about pH 4 to 7 for serine alkaline proteinase. Typical buffer solutions include sodium pyrophosphate buffer solution, citric acid buffer solution, acetic acid buffer solution, or Tris-HCl buffer solution.

The esterase used in the invention is a serine alkaline proteinase. These enzymes exhibit high esterase activity and selectively act on aromatic amino acids. Typical serine alkaline proteinases include subtilisin and alkaline proteinases from various strains of Bacillus Aspergillis, Streptomyces, Penicillium, and Arthorobacter. A preferred serine alkaline proteinase is subtilisin Carlsberg which is commercially available. A catalytic amount of enzyme is employed in the reaction process preferably 10–500 mg per 1 mmole of α-L-aspartyl-L-phenylalanine or N-protected-α-L-aspartyl-L-phenylalanine. A calcium salt may also be added to aid enzyme activity.

The enzyme may be present in the free state or may be immobilized by binding to a suitable support such as porous glass, polyacrylamide gel, carboxylmethyl cellulose, or aminoethyl cellulose. "IMMOBILIZED ENZYMES", Vol. 44, METHODS IN ENZYMOLOGY, ed. Klaus Mosback, discusses various methods of enzyme immobilization.

The reaction temperature employed is usually in a range of 10°–50° C., which is sufficient to maintain enzyme activity. A preferred range is 20°–40° C.

The reaction is conducted in a medium of water and alcohol in which the alcohol concentration is sufficient to reverse the esterase activity of the enzyme. The alcohol concentration may be 10–90% by volume. A preferred alcohol concentration is 30–70% by volume. A more preferred alcohol concentration is 50–60% with 60% alcohol by volume being optimal.

In an especially preferred embodiment of the invention the serine alkaline proteinase is subtilisin Carlsberg, a proteinase having specific esterase activity, and the alcohol is methanol which is present in a concentration of 60% by volume. The aqueous-alcohol mixture contains 5.0 mM calcium chloride and has a pH of 5.0, and the reaction is conducted at a temperature of 25° C.

The reaction proceeds smoothly under these conditions until completed. A preferred reaction period time is 1 to 260 hours. A more preferred reaction period time is 1–90 hours. The reaction product is conveniently separated from the reaction system by standard chromatographic techniques and other methods recognized in the art.

The invention will appear more fully from the examples which follow. These examples are given by way of illustration and are not to be construed as limiting the invention either in spirit or in scope, as many modifications both in materials and methods will be apparent to those skilled in the art. In the examples temperatures are given in degrees Centigrade (°C.) and quantities of materials in parts by weight unless otherwise specified. The relationships between parts by weight and parts by volume is the same as that existing between grams and milliliters.

EXAMPLE 1

Subtilisin Carlsberg (Protease Type VIII, Sigma Chemical Co.) is dissolved in distilled water at a concentration of 40 mg/ml and is dialyzed against distilled water at 5° C. 0.1 Parts by volume of the enzyme solution is mixed with 0.9 parts by volume of an aqueous-methanol solution containing 0.0056 parts by weight of α-L-aspartyl-L-phenylalanine. The aqueous-methanol solution is prepared by mixing 0.6 parts by volume of methanol with 0.075 parts by volume of 0.33 M sodium acetate, 0.225 parts by volume of 0.33 M acetic acid and 0.002 parts by volume of 2.5 M calcium chloride. Before adding the enzyme, the aqueous-methanol solution is sonicated for one minute in order to disperse the α-L-aspartyl-L-phenylalanine. The overall pH is adjusted to pH 5.0 with dilute hydrochloric acid. The final reaction mixture containing 4 mg/ml of enzyme, 5.0 mM calcium chloride, 0.1 M acetic acid buffer, 60% methanol, and 0.02 M α-L-aspartyl-L-phenylalanine is allowed to react at about 25° C. with continuous agitation for a period of four days. The reaction mixture is run through a Sephadex LH-20 column to separate the enzyme from the dipeptide. The dipeptide fractions are pooled and treated with hydrohalide according to U.S. Pat. Nos. 3,798,207 and 4,173,562 in order to precipitate and purify α-L-aspartyl-L-phenylalanine methyl ester of formula III.

EXAMPLE 2

The process of example 1 is repeated except that immobilized enzyme is used as the catalyst. The enzyme is covalently immobilized to cyanogen bromide-activated DEAE cellulose. The DEAE cellulose (preswollen DE52, Whatman) is activated by washing 0.075 parts by weight with 0.1 M sodium bicarbonate and then reacting with 3 parts by volume of cyanogen bromide solution (25 mg/ml). The pH is adjusted and maintained at 11.0 with 2 M sodium hydroxide and stirred gently for 6 minutes at 25° C. The gel is filtered and washed with 100 parts by volume of 0.1 M sodium bicarbonate. 0.025 parts by weight of subtilisin Carlsberg, dissolved in 0.25 parts by volume of 0.1 M sodium bicarbonate and dialyzed 4 hrs. v.s. the same buffer at 5° C., is mixed with a cyanogen bromide-activated gel in a closed polypropylene tube (under argon) at 5° C., for 17 hr. The bound enzyme is then washed with distilled water and reacted with 5 parts by volume of 1 M ethanolamine (pH 9.0) with gentle stirring for 2 hrs. at 25° C. The gel is washed twice with distilled water and resuspended in 0.3 parts by volume of distilled water. This immobilized enzyme suspension is mixed with 0.7 parts by volume of an aqueous/methanol mix such that the final reaction mix contains the same concentration of materials as in Example 1. The reaction is carried out as in Example 1 except that the immobilized enzyme is removed by centrifugation prior to purification of the product.

EXAMPLE 3

Substitution of an equivalent quantity of ethanol for the methanol of Example 1 and 2 and substantially following the procedures outlined therein affords α-L-aspartyl-L-phenylalanine ethyl ester of formula IV.

EXAMPLE 4

Substitution of 0.0125 parts by weight of N-carbobenzoxy-α-L-aspartyl-L-phenylalanine for the α-L-aspartyl-L-phenylalanine of Example 1 and 2 and substantial repetition of the procedures detailed therein provides N-carbobenzoxy-α-L-aspartyl-L-phenylalanine methyl ester. Reduction of this compound by the method of M. Bergmann and L. Zervas. Ber. 65: 1192 (1932) removes the N-protecting carbobenzoxy group to give α-L-aspartyl-L-phenylalanine methyl ester.

CHART A

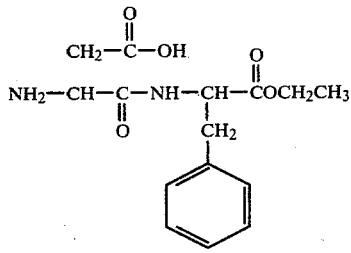

What I claim is:

1. A process for esterifying α-L-aspartyl-L-phenylalanine which comprises contacting α-L-aspartyl-L-phenylalanine with an alcohol in the presence of an effective amount of a proteolytic enzyme with specific esterase activity in an aqueous alcohol medium at a pH of 4 to 7 in which the alcohol concentration is sufficient to reverse the hydrolytic activity of the protease.

2. A process according to claim 1 wherein the proteolytic enzyme with specific esterase activity is a serine alkaline proteinase.

3. A process according to claim 2 wherein the serine alkaline proteinase is subtilisin Carlsberg.

4. A process according to claim 2 wherein the alcohol is methanol in a concentration of 10–90%.

5. A process according to claim 4 wherein the serine alkaline proteinase is subtilisin Carlsberg.

6. A process for esterifying α-L-aspartyl-L-phenylalanine which comprises contacting α-L-aspartyl-L-phenylalanine with methanol in the presence of subtilisin Carlsberg serine alkaline proteinase in an aqueous-methanol medium at a pH of 5.0 in which the methanol concentration is 60%.

7. A process for esterifying α-L-aspartyl-L-phenylalanine which comprises contacting N-protected-α-L-aspartyl-L-phenylalanine with an alcohol in the presence of an effective amount of a protease with specific esterase activity in an aqueous-alcohol medium at a pH of 4 to 7 in which the alcohol concentration is sufficient to reverse the hydrolytic activity of the protease followed by removal of the N-protecting group.

8. A process according to claim 7 wherein the proteolytic enzyme with specific esterase activity is a serine alkaline proteinase.

9. A process according to claim 8 wherein the serine alkaline protease is subtilisin Carlsberg.

10. A process according to claim 7 wherein the alcohol is methanol in a concentration of 10–90%.

11. A process according to claim 10 wherein the serine alkaline proteinase is subtilisin Carlsberg.

12. A process for esterifying α-L-aspartyl-L-phenylalanine which comprises contacting N-carbobenzoxy-α-L-aspartyl-L-phenylalanine with methanol in the presence of subtilisin Carlsberg serine alkaline proteinase in an aqueous-methanol medium at a pH of 5.0 in which the methanol concentration is 60% followed by removal of the carbobenzoxy protecting group.

* * * * *